United States Patent [19]
Trotta et al.

[11] Patent Number: 5,290,306
[45] Date of Patent: Mar. 1, 1994

[54] PUNCTURE RESISTANT BALLOON CATHETER

[75] Inventors: Thomas Trotta, Miami, Fla.; Jeffrey A. Johnson, Bartlesville, Okla.

[73] Assignee: Cordis Corporation, Miami Lakes, Fla.

[21] Appl. No.: 442,568

[22] Filed: Nov. 29, 1989

[51] Int. Cl.⁵ ............................................. A61M 29/02
[52] U.S. Cl. ..................................... 606/194; 604/96
[58] Field of Search ............................. 604/96–103, 604/265; 606/191, 192, 194, 195

[56] References Cited

U.S. PATENT DOCUMENTS

| | | | |
|---|---|---|---|
| 3,045,677 | 7/1962 | Wallace | 604/101 |
| 3,814,137 | 6/1974 | Martinez . | |
| 3,889,685 | 6/1975 | Miller, Jr. et al. . | |
| 3,924,634 | 12/1975 | Taylor et al. | 604/100 |
| 4,141,364 | 2/1979 | Schultze . | |
| 4,195,637 | 4/1980 | Gruntzig et al. . | |
| 4,323,071 | 4/1982 | Simpson et al. . | |
| 4,338,942 | 7/1982 | Fogarty . | |
| 4,351,341 | 9/1982 | Goldberg et al. | 604/96 |
| 4,406,656 | 9/1983 | Hattler et al. . | |
| 4,479,497 | 10/1984 | Fogarty et al. . | |
| 4,553,545 | 11/1985 | Maass et al. . | |
| 4,573,966 | 3/1986 | Weikl et al. | 604/53 |
| 4,606,347 | 8/1986 | Fogarty et al. . | |
| 4,705,709 | 11/1987 | Vailancourt | 604/265 |
| 4,732,152 | 3/1988 | Wallsten et al. . | |
| 4,763,653 | 8/1988 | Rockey . | |
| 4,776,337 | 10/1988 | Palmaz . | |
| 4,795,458 | 1/1989 | Regan | 623/1 |
| 4,800,882 | 1/1989 | Gianturco . | |
| 4,811,737 | 3/1989 | Rydell . | |
| 4,906,237 | 3/1990 | Johansson et al. | 604/265 |
| 4,923,450 | 5/1990 | Maeda et al. | 604/265 |
| 4,933,178 | 6/1990 | Capelli | 604/265 |

OTHER PUBLICATIONS

"Expandable Intrahepatic Portacaval Shunt Stents", Palmaz et al. AJR: 145", pp. 821–825, Oct. 1985.
"Expandable Intraluminal Graft: A Preliminary Study", Palmaz et al., vol. 156, No. 1, pp. 73–77.
"The Palmaz Stent: A Possible Technique for Prevention of Postangioplasty Restenosis", Levin, vol. 169, pp. 873–874, Radiology, Sep. 1988.
"Intraluminal Stents in Atherosclerotic Iliac Artery Stenosis: Preliminary Report of a Multicenter Study", Palmaz et al., vol. 168, pp. 727–731, Radiology, Sep. 1988.

*Primary Examiner*—C. Fred Rosenbaum
*Assistant Examiner*—Michael Rafa
*Attorney, Agent, or Firm*—Gerstman & Ellis, Ltd.

[57] ABSTRACT

A balloon catheter having an inflatable balloon in which the outer surface of the inflatable balloon is surrounded by an elastomeric sleeve. The sleeve is attached throughout at least a majority of its area to the balloon outer surface to provide pin hole and abrasion resistance. Preferably, the inflatable balloon is made of a flexible material of less elasticity than the material of the elastomeric sleeve. Thus the balloon expands to a generally limited maximum transverse dimension, while the collapse of the balloon is facilitated by the elastomeric sleeve.

2 Claims, 1 Drawing Sheet

PUNCTURE RESISTANT BALLOON CATHETER

BACKGROUND OF THE INVENTION

Balloon catheters are well-known devices in which the catheter carries an inflatable balloon to occlude and seal a body space, to expand a blood vessel through pressurized inflation of the balloon, or for any other desired purpose which may typically but not necessarily be a therapeutic purpose in the medical field. In the case of dilatation balloon catheters for angioplasty, for example a PTCA procedure, the catheter balloon is generally made out of a thin, strong material which is of relatively low resilience. For example, the catheter balloon may be made out of biaxially oriented polyethylene terephthalate (PET) or a polyamide material such as nylon. Such strong, flexible materials are commonly used for angioplasty balloons, and have the advantage that they are flexible but inelastic so that they can expand outwardly to a predetermined diameter, and then cease further expansion at normal pressures, to avoid damage to the artery wall by over expansion.

One difficulty which is found with such biaxially oriented balloons is that, since they are typically very thin-walled, they can be easily punctured through abrasion or the like, even though they have a high tensile strength. Thus, pin holes and ruptures are fairly common when such catheter balloons are used in contact with rough surfaces. Also, tiny flaws in the mold of such balloons can create weak spots, since the balloons are so thin-walled. However, it is impractical to increase the wall thickness of these biaxially oriented materials, since then they become too stiff, with high flexural moduli, with the result that such balloons do not collapse properly on deflation to facilitate easy withdrawal from the vascular system of a patient.

Accordingly, there is a need for a balloon catheter in which the catheter balloon is strong and relatively inelastic, without being subject to the formation of pin holes in the molding process, or tears in the balloon wall through abrasion. At the same time, the balloon must still be easily collapsible down to a small diameter upon deflation.

Also, there is a need to provide such catheter balloons with an improved lubricity, or for them to be facilitated to carry a therapeutic agent such as an anticoagulant, particularly in the case of angioplasty balloons.

DESCRIPTION OF THE INVENTION

In this invention, a balloon catheter is provided which comprises a flexible, elongated member, an i balloon carried on the elongated member to define an inflation chamber within the balloon, and an inflation conduit extending along the member and communicating with the inflation chamber.

In accordance with this invention, the inflatable balloon has an outer surface which is surrounded by an elastomeric sleeve. The sleeve is bonded typically throughout at least a majority of its area to the balloon outer surface, to provide pin hole and abrasion resistance.

Preferably, the elastomeric sleeve and balloon are defined as a multiple layer tube, coextruded together to form a single, integral member of two concentric, telescoping layers. It is also preferable for the inflatable balloon to be made of a flexible material which is of less elasticity than the material of the elastomeric sleeve.

Thus, the inflatable balloon, being preferably biaxially oriented polyester such as PET, or a polyamide such as nylon, is flexible but relatively inelastic, to limit the maximum transverse dimensions of the inflated balloon for reasons such as that mentioned above.

The elastomeric sleeve is then provided as an outer layer, and typically serves as an aid for the deflation of the balloon once again, after the pressure within the balloon is released. The natural, resilient character of the elastomeric sleeve causes compression of the non-resilient balloon back to a deflated, minimum-diameter condition, being driven by the natural contraction of the stretched elastomeric sleeve back toward its original configuration. Thus, as an advantage of the balloon catheter of this invention, the undesirable characteristic of "winging", in which the inflatable balloon collapses on deflation into an enlarged-width, flat configuration, is reduced or eliminated by the presence of the surrounding elastomeric sleeve, without creating undue stiffness in the balloon.

At the same time, any pin holes that may have been formed in the inflatable balloon are sealed by the surrounding elastomeric sleeve, so that the loss of inflation fluid through the pin hole, if it exists, will be negligible or non-existent. At the same time, the elastomeric sleeve serves as an outer protective coating to the balloon, with the elastomeric material being far more resistant to abrasion and rough handling than the ultra-thin, flexible, inelastic, inflatable balloon. Thus the accidental creation of rips or tears is greatly reduced as well.

The outer layer of elastomeric material may be made of any elastomer, for example, polyurethanes, polyester-ether copolymers, or polyetheresteramide terpolymers. It is often preferable to select an elastomeric sleeve component which is more compatible with a hydrogel formulation or the like which can serve as a lubricant to the surface of the balloon catheter. Thus, a catheter of improved lubricity for ease of insertion, typically into the arteriovenous system of a patient, may be provided if it carries such a hydrogel coating. Materials such as polyurethane are more compatible to receiving many lubricating hydrogel formulations and retaining it on its surface than are materials such as PET or polyamide.

Additionally, the outer surface of the elastomeric sleeve may carry a layer of material comprising a therapeutic agent or a lubricating agent or both, in a manner similar to the disclosures of Rowe et al. U.S. patent application Ser. No. 322,929 filed Mar. 14, 1989, commonly owned with this application.

The elastomeric sleeve may comprise a material having an elongation to break of at least 100 percent and a Shore 'D' durometer of no more than substantially 55 to assure that the material is relatively soft. The relatively inelastic balloon material, however, may have an elongation to break of typically no more than 30 percent. Such materials generally are substantially stiffer, having a Shore 'D' durometer of at least about 70.

As further modification, the elastomeric sleeve may comprise a formulation which is an intimate physical mixture of, typically, 50 to 98 weight percent of a structural plastic material (such as polyurethane elastomer) and 2 to 50 weight percent of poly(ethylene oxide) or another friction reducing agent. The friction reducing agent can migrate out of its intimate physical relation with the structural plastic material so that the elastomeric sleeve serves a double function of the physical performance of the elastomeric sleeve as described above, coupled with the friction reducing performance, which is more fully described in Rowland et al. U.S. patent application Ser. No. 345,102, filed Apr. 28, 1989 and entitled Hydrophilic Friction Reducing Coating commonly owned with this application.

If desired, the balloon catheter of this invention may carry an expansible stent about the outer surface of the elastomeric sleeve, so that the expansible stent may be expanded by the balloon into engagement with the wall of a blood vessel. In this and other instances, the elastomeric sleeve may desirably carry an antithrombogenic agent or the like as more particularly described in the pending Rowe et al. application.

One may inflate and longitudinally stretch a coextruded tube of the balloon and outer elastomeric coating with heat setting, to biaxially orient the balloon.

Alternatively, the balloon catheter of this invention may carry an inflatable balloon with an outer, adhering elastomeric sleeve which is not coextruded as described above, but rather the elastomer may be provided to the pre-formed balloon as a solvent dispersion. Following drying of the solvent dispersion, the elastomer layer is formed.

As another manufacturing alternative, the inflatable balloon may be inflated into pressurized contact with the outer tube of elastomeric material, and then heated and biaxially oriented by stretching, with the result that the balloon also enters into adhering contact with the elastomeric outer tube as it is biaxially oriented.

A PET balloon may be dip coated with a polyurethane elastomer solution. The resultant coating and balloon may have the functional performance of a PET balloon with the added protection of the polyurethane elastomeric layer. This layer can provide improved scuff and abrasion resistance to the typically thin-walled balloon, and also the polyurethane outer layer may assist in the collapse of the balloon after deflation, avoiding "winging" and other problems resulting from excessive transverse dimensions of the collapsed balloon. Similarly, balloon pin holes are sealed by the polyurethane layer with greatly increased reliability, since a pin hole will only have a negative effect if both layers exhibit aligned pin holes. Separate pin holes in either or both of the layers which do not register with each other will generally have no negative effect since there can be no significant leakage through the walls upon balloon inflation in that circumstance.

Alternatively, a different biaxially oriented material such as nylon 12 may be used as the balloon, with a polyetheresteramide terpolymer serving as the outer elastomeric layer, to achieve advantages similar to those of the previous embodiment.

It is generally desirable to select elastomeric materials that are at least somewhat adhesively compatible to the material of which the balloon is fabricated, so that adhesion may be provided between the two layers.

DESCRIPTION OF SPECIFIC EMBODIMENTS

Figure 1:
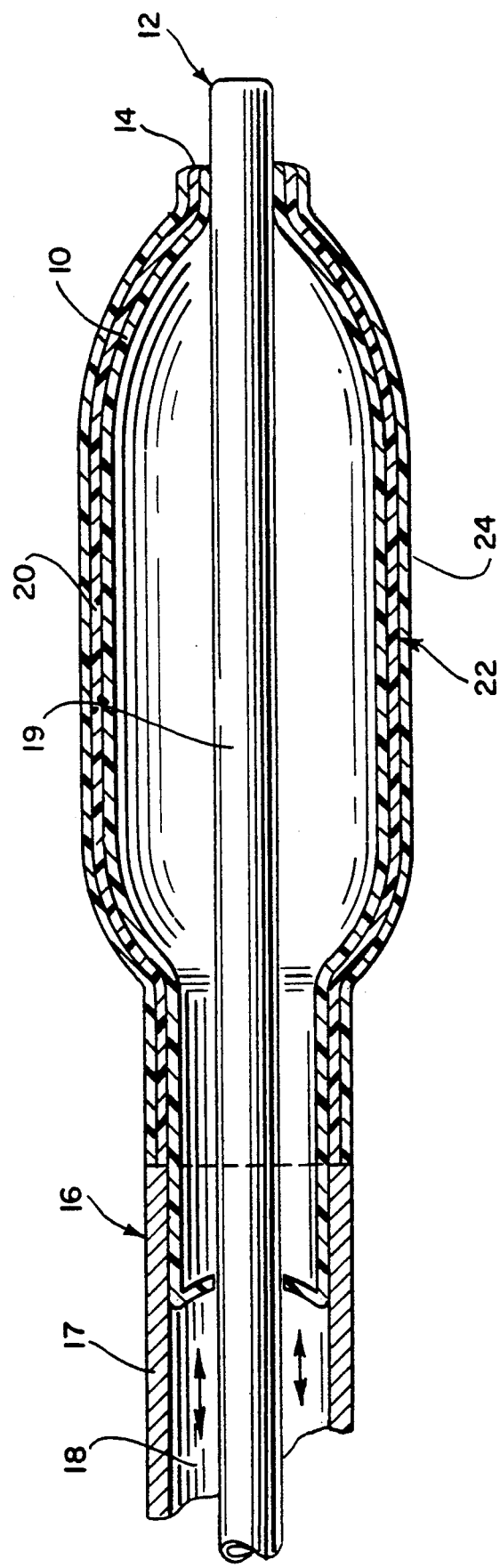
FIG. 1 is an enlarged, fragmentary view, taken partly in longitudinal section, of the distal end of a balloon catheter in accordance with this invention.

In the drawing, balloon 10 is carried at the distal end of catheter 12, which catheter may be of any conventional design of the prior art except for the modifications specifically disclosed herein. For example, the specific catheter shown may be used for a conventional PCTA procedure, using balloon 10 to expand the inner diameter of an occluded coronary artery.

As is conventional, balloon 10 may be made of a cylindrical plastic member which is typically biaxially oriented, for example PET or nylon. Balloon 10 is sealed at its respective ends 14, 16 to an outer catheter tube 17 and an inner catheter 19, as shown. Inflation lumen 18 may be conventionally provided for fluid inflation and deflation of balloon 10, being a space between outer catheter tube 17 and inner catheter 19. Inner catheter 19 may or may not carry one or more catheter lumens, as may be desired. Additionally, catheter 12 may carry electrodes and electrical conductors extending the length thereof for purposes of pacing or sensing of coronary action, if desired.

If desired, means for venting air from catheter balloon 10 may be provided.

The wall thickness of balloon 10, when made of biaxially oriented PET, may be about 0.0005 inch. Catheter 12 and catheter tubing 17 may each be made of a polyester such as DuPont Hytrel. Balloon 10 may be sealed to catheter 12 and catheter tubing 17 at its respective ends with an adhesive or by a heat sealing process in a conventional manner.

In accordance with this invention, balloon 10 comprises the inner layer of a co-extruded tubing, with the outer tubular layer 20 thereof comprising a polyurethane elastomer, many of which are commercially available and used in the manufacture of catheters.

Coextruded polyurethane elastomer outer layer 20 is bonded through the coextruded manufacturing process to the inner PET balloon layer 10. Outer polyurethane layer 20 may have a thickness of, typically, 0.0005 to 0.002 inch, to provide abrasion and puncture resistance to the coextruded tubular structure 22 which comprises PET balloon 10 and polyurethane outer tubular layer 20. The polyurethane elastomer layer 20 is substantially more soft and elastic than the PET balloon layer 10. The PET balloon 10 generally expands to a fully expanded configuration and then greatly resists further expansion at even substantially increased internal pressures. However, the elastomeric layer 20 stretches outwardly upon such expansion, and thus provides a transversely collapsing bias to balloon 10 upon deflation. Despite the increased wall thickness provided by outer layer 20, the tubular balloon structure 22 retains the desired characteristics of a biaxially oriented PET balloon without excessively increased stiffness upon deflation. Outer elastomer layer can compress inner balloon 10 upon deflation, as the outer elastomeric layer collapses back towards its normal, unstressed configuration following balloon inflation, to assist in a desired, complete collapse of the balloon structure 22.

If desired, a third hydrogel layer 24 may be provided to balloon structure 22, to serve as a lubricant for insertion of the catheter. This layer also may be very thin, typically 0.0001 to 0.0005 inch. Layer 24 may also include a therapeutic agent such as an anticoagulant.

The above has been offered for illustrative purposes only, and is not intended to limit the scope of the invention of this application, which is as defined in the claims below.

That which is claimed is:

1. A balloon catheter, which comprises a flexible, elongated member, an inflatable balloon carried on the elongated member to define an inflation chamber within said balloon, and an inflation conduit extending along said member and communicating with the inflation chamber, said inflatable balloon being surrounded by an elastomeric sleeve to provide pinhole and abrasion resistance to said balloon, said balloon and sleeve being together defined by a coextruded tube, said balloon being made of a flexible, relatively inelastic, biaxially oriented material selected from the group consisting of PET and nylon.

2. A balloon catheter, which comprises a flexible, elongated member, an inflatable balloon carried on the elongated member to define an inflation chamber within said balloon, and an inflation conduit extending along said member and communicating with the inflation chamber, said inflatable balloon being surrounded by an elastomeric sleeve to provide pin hole and abrasion resistance to said balloon, said elastomeric sleeve being made of a material selected from the group consisting of polyurethane and polyetheresteramide terpolymer, said balloon and sleeve being together defined by a coextruded tube, said balloon being made of a flexible, relatively inelastic biaxially oriented material selected from the group consisting of PET and nylon.

* * * * *